United States Patent [19]

Shepherd et al.

[11] 3,941,858

[45] Mar. 2, 1976

[54] HYDROPHILIC POLYMERS, ARTICLES AND METHODS OF MAKING SAME

[75] Inventors: Thomas H. Shepherd; Francis E. Gould, both of Princeton, N.J.

[73] Assignee: National Patent Development Corporation, New York, N.Y.

[22] Filed: Aug. 7, 1973

[21] Appl. No.: 386,430

Related U.S. Application Data

[60] Division of Ser. No. 654,044, July 5, 1967, abandoned, Continuation-in-part of Ser. No. 567,856, July 26, 1966, Pat. No. 3,520,949.

[52] U.S. Cl. .......................... 260/885; 3/1; 3/1.4; 3/1.5; 260/2.5 R; 260/2.5 EP; 260/2.5 N; 260/8; 260/27 R; 260/29.1 SB; 260/33.6 UA; 260/42.21; 260/86.1 E; 260/837 R; 260/844; 260/857 UN; 260/857 G; 264/1; 264/183; 264/210 R; 351/160; 351/177
[51] Int. Cl.$^2$.. C08K 3/24; C08K 5/01; C08L 31/02
[58] Field of Search .......... 260/86.1 E, 86.1 R, 885, 260/33.6 UA, 29.1 SC, 29.1 SB

[56] References Cited
UNITED STATES PATENTS

| | | | |
|---|---|---|---|
| 2,558,139 | 6/1951 | Knock et al. | 260/86.1 E |
| 2,861,965 | 10/1958 | Roncoroni | 260/33.6 UA |
| 3,220,960 | 10/1965 | Wichterle et al. | 260/2.5 |

FOREIGN PATENTS OR APPLICATIONS

| | | |
|---|---|---|
| 703,377 | 2/1965 | Canada |

OTHER PUBLICATIONS
Refojo et al., "Jour. of Applied Polymer Science," Vol. 9 (1965), pp. 2425–2435.

*Primary Examiner*—Murray Tillman
*Assistant Examiner*—J. Ziegler
*Attorney, Agent, or Firm*—Cushman, Darby & Cushman

[57] ABSTRACT

A process for preparing hydrophilic cross-linked polymers and products prepared thereby, said process comprising admixing in a solvent-free system in the presence of a free radical, vinyl polymerization catalyst and reacting a major amount of a water-soluble polymerizable monoester of an olefinic acid having at least one substituted functional group with a minor amount of a polymerizable diester of one of said olefinic acids having at least two esterifiable hydroxyl groups. The novel products include a solid friable foam which can be disintegrated to powder. Shaped bodies can be prepared in the form of articles which can be cast with additives such as fragrances, medicinals, flavors, chemicals and the like, which are gradually released from the article when it is wetted in water or alcohol. Liquid casting syrups adapted to be polymerized in situ with or without additives can be formed. The casting syrups can be prepared in water to yield a polymer soluble in alcohol which is suitable for formation of hydrophilic coatings as by spray, dip, casting and the like.

10 Claims, No Drawings

HYDROPHILIC POLYMERS, ARTICLES AND METHODS OF MAKING SAME

This application is a division of application Ser. No. 654,044 filed July 5, 1967 and now abandoned and is a continuation-in-part of application Ser. No. 567,856 filed July 26, 1966 and now U.S. Pat. No. 3,520,949.

This invention relates to novel hydrophilic polymers and processes of making same and has particular relation to such hydrophilic polymers in the form of casting syrups, friable solid foams and in powdered form, the latter form being particularly adapted as a carrier for medicinally-active substances and for natural and synthetic flavors, essences, fragrances, spices, food colors, sweeteners, dyes and the like.

It is known to produce hydrophilic polymers, particularly to produce cross-linked hydrophilic polymers and, more particularly, to produce same in the form of shaped body hydrogels in an aqueous solution by copolymerization whereby a major portion of a monoester of acrylic or methacrylic acid with a bi-functional alcohol which has an esterifiable hydroxyl group and at least one additional hydrophilic functional group is copolymerized in aqueous solution with a small amount of a diester of these acids and of an alcohol which has at least two esterifiable hydroxyl groups (see U.S. Pat. Nos. 2,976,576 and 3,220,960).

It is known that said prior art shaped body, hydrophilic polymers prepared in an aqueous system are carriers for medicinally-active substances. Thus, it is known that medicinally-active substances may be dissolved in the aqueous constituent of such prior art shaped body hydrogels to provide gradual release of the medicinally-active substances; however, the resulting solutions are difficult to handle and store and the medicinal components are susceptible to air oxidation, degradation, deterioration, evaporation, etc.

Heretofore, it has been necessary prepare a solid or shaped body of the hydrophilic polymer and thereafter dissolve in the aqueous constituents of such shaped body the medicinal flavor, sweeteners, coloring agent and the like. Additionally, in the prior art preparation, employing copolymerization in an aqueous solution, it has not been possible to directly prepare a foam by the addition of the usual foaming agents, such as sodium bicarbonate, for the reason that a soft semi-gelatinous hydrogel product resulted rather than the desired hard friable foam and it was not possible to convert such semi-gelatinous product to a friable foam or to a compactable powder.

In addition, the said prior art process employing the conventional redox catalyst such as sodium bicarbonate and ammonium persulfate, potassium sulfate, sodium thiosulfate and ammonium persulfate or potassium sulfate, caused the polymerization reaction to go to completion at temperatures above 0°C. thereby preventing the preparation of a prepolymer preferably in the form of a liquid casting syrup which is capable of being dyed, pigmented, thickened and otherwise varied in form and thereafter cured to form solid or shaped bodies such as rods, sheets, tubes and other molded articles, or a hard, friable foam as will be hereinafter further described.

Additionally, said prior art process has resulted in an incompletely (up to about 95%) polymerized polymer and has further resulted in a polymer capable of absorbing excess amounts (more than 30% and up to 80% by weight) when fully equilibrated in aqueous solutions.

The novel hydrophilic polymers of the present invention prepared in a water-free state, are substantially completely (about 99.5%) polymerized and are incapable of absorbing more than up to about 30% by weight of water when equilibrated in aqueous solution.

It now has been found that hydrophilic polymers can be prepared in a water-free system so as to permit the direct preparation of liquid casting syrups in prepolymer form which can be used for direct in situ polymerization in the form of castings of shaped bodies, films and coatings, which can be treated with conventional foaming agents such as sodium bicarbonate to result in hard, friable foams which can be directly formed into the swelled state or ground directly to powder form.

It also has been found that hydrophilic polymers can be prepared in a water-free system so as to permit ready preparation of the hydrophilic polymer products in powdered form. An object of the present invention is to prepare said hydrophilic polymers in a water-free system to permit their direct conversion to a powdered foam whereby the powdered polymers are especially adapted as carriers for medicinally-active substances, natural or synthetic flavors, essences, fragrances, spices and the like. The polymeric powders of the present invention have been found to be compact in form and have been found to provide the necessary stability and shelf life to enable their use as carriers for medicinal and flavoring substances which are susceptible to chemical reactions such as air oxidation, deterioration, evaporation and degradation.

A further advantage derived from the compactness ability of the instant powdered hydrophilic polymers is that upon encapsulation of the said powder carrying medicinally-active substances, flavors, essences and the like, greater stability and longer shelf life are provided than was heretofore possible.

Polymeric powders containing encapsulated flavors, essences or spices can be reconstituted in solution at will, thus providing superior flavoring solutions because encapsulation prevents air deterioration of the flavoring component and also prevents losses due to evaporation.

The liquid casting syrups of this invention are prepared by mixing a major amount of suitably purified commercial polymerizable monoester of an olefinic acid containing at least one substituted hydrophilic functional group with a minor concentration of a free-radical catalyst and heating from ambient temperature to 80°C. until the polymerized portion of the monomer no longer shows water solubility. This product is then cooled to room temperature and addition of theoretical catalyst content carried out. The casting syrup can then be suitably dyed and pigmented and the fluid viscosity increased as desired by addition of appropriate thickening agents.

The casting syrup can then be cured to form products capable of being cast, formed or machined into rods, sheets, etc., for various uses. The product can exist in a rigid state, swelled state or as a foam. The polymer obtained from the cured casting liquids has good mechanical strength, reversible fluid absorption properties, the ability to retain its shape in a fluid media and to elastically recover it after deformation.

The casting syrup is also suitable, for example, for in situ polymerization in dental prosthesis, particularly for use in the preparation of denture liners and mouth guards. The absorbent qualities of the cured product permit advantageous use in other medical-surgical applications such as heart valves, vessel substitutes, dializer diaphragms, intrauterine devices and the like.

Prior to the addition of dyes, pigments, thickening agents, or other additive components, the liquid casting syrups are added to an excess quantity of water to form a precipitated polymer. The latter is soluble in highly polar organic solvents such as alcohols, glycols and glycol ethers. The precipitated polymer, when dissolved in polar solvents, is used as a polymer solution for the formation of films, coatings and the like. Alternately, the precipitated polymer is dried and used for fabrication of shaped articles, by casting, injection molding, extrusion, calendaring and the like.

In a further embodiment of the invention, hydrophilic soluble thermoplastic polymers are prepared by suspension polymerization of hydroxy ethyl methacrylate in a non-polar medium such as silicone oil or mineral oil. The monomer containing catalyst is dispersed in the non-polar medium in the form of small droplets which polymerize to form finely divided spheres or beads. Such beads may be dissolved in polar organic solvents for the preparation of films, coatings and the like. Also, the beads may be used directly in the fabrication of thermoplastic shaped articles as by injection molding, extrusion, calendaring and the like. Suspension polymerization, preferably, is conducted in an oil bath at temperatures ranging from 50° – 150°C. until bead formation is completed. The ratio of suspension oil to monomer preferably is from about 5:1 to about 20:1. The catalyst to monomer ratios preferably range from about 0.05 to 1.0 per 100 parts monomer.

The hydrophilic polymers of the present invention, polymerized in the water-free state, can be formed to adhere to metal, glass, rubber, plastics and other surfaces. Also, they can be cast into solid bodies which can be formed and ground into toric contact lens, which heretofore has not been possible with hydrophilic polymers polymerized in aqueous solution.

Starting materials which may be utilized in accordance with the present invention are hydroxy alkyl esters of an alpha-beta unsaturated carboxylic acid such as 2-hydroxy ethyl methacrylate, hydroxy propyl methacrylate and the like. These are admixed in a water-free system with appropriate quantities of a free radical catalyst such as tertiary butyl peroctoate, isopropyl percarbonate, benzoyl peroxide, and the like and a suitable cross-linking monomer such as ethylene glycol dimethacrylate, 1,3-butylene dimethacrylate, 1,4-butylene dimethacrylate or other polyfunctional monomeric esters.

Free radical catalyst concentrations in the range of 0.05 g. to 1 g. catalyst per 100 g. of polymerizable hydroxy alkyl ester have been found to be adequate with the preferred quantity being between 0.1 and 0.2 per 100 g. starting material.

The mechanical properties imparted to the polymer of the invention and its ability to retain water as a homogeneous constituent are strongly influenced by the proportion of polyfunctional cross-linking agent present. For the polymer of this invention, concentrations of 0.05 to 15 g./100 g. of 2-hydroxy ethyl methacrylate have been found convenient, the preferred range being 0.1 to 0.2 g. cross-linking agent per 100 g. of polymerizable hydroxy alkyl ester.

Polymerization of the above reactants may be accelerated by the application of heat or, by selecting the catalyst and the amount thereof, the application of heat may be omitted and rapid polymerization induced at ambient temperatures. In instances where heat is applied for curing, temperatures ranging from about 20° to about 150°C. have been found to be convenient with 40° to 70°C. being the preferred range.

Another object of the present invention is to produce new properties, as set forth above, and to improve and upgrade existing properties of the base hydrophilic polymer material by the incorporation therewith of a minor amount of one or more additive components selected from the group consisting of resins, rosin esters, phenoxy resins, silicone resins, low molecular weight polyisobutylenes, synthetic polymers and prolamines. The new compositions are especially adapted to form polyblends, which produce new properties and improve and upgrade existing properties of the base hydrophilic polymer.

The mixture is heated or otherwise cured in the absence of compatible volatile or non-volatile organic solvents to produce thermosetting polymeric materials having properties superior to those of the major constituent of the formulation. The upgraded properties of these new compositions of matter include, but are not necessarily limited to, improved hardness, adhesion, abrasion resistance, resiliency, and toughness. The polymerized material will yield products with improved machining and polishing characteristics and may also find use as a molding powder or polyblended with other molding compounds. Other slight property improvements can be effected through use of small amounts of other crosslinking glycol dimethacrylate.

The method of this invention may be used to produce thermosetting surface coatings with improved adhesion to various substrates or to produce thermosetting resins for use as sheetings and films with improved clarity and toughness.

In general, 2-hydroxy ethyl methacrylate and the cross-linking monomer ethylene glycol dimethacrylate in quantities ranging from 10 to 50% by weight (preferred range of 50%) is mixed with 90–50% by weight of a commercially available resin of the coumarone indene type or their phenol modified counterparts in the presence of a free radical catalyst such as tertiary butyl peroctoate, isopropyl percarbonate, etc., and heated at temperatures ranging from 40° to 200°C. for approximately 30 minutes. Organic or inorganic solvents are used as necessary to increase compatibility of the components. Compatible polymers having improved properties of tensile strength, modulus, hardness, thermal conductivity, etc., are formed. The foregoing preferred proportional limitations also are employed with the phenoxy resin and the silicone resin additive components.

The resulting polymers can be prepared in the form of films or rods suitable for grinding into fine powders. By admixing foaming agents such as sodium bicarbonate with the reactants prior to curing, the polymer may be obtained in the form of a foam which is easily disintegrated into a fine powder by means of a shearing action. The polymeric powders of this invention are preferably obtained from foams. Quantities of 1 to 10 grams foaming agent per 100 grams of reactants have been found to be sufficient.

Polymeric powders prepared by any of the above means are mixed with natural or synthetic flavors or essences dissolved in an appropriate solvent and the mixture placed on a mechanical roller so that the solution becomes intimately mixed. The solution is then filtered and dried by air evaporation or forced heat. Upon evaporation of the solvent the flavoring or essence is retained by the powder. Due to its extreme hydrophilicity and because the hydrophilic polymer of this invention has reversible fluid adsorption properties, the powders can be reconstituted in solution at will to provide solutions which give concentrated flavors or essences.

Vessel substitutes for humans made from plastics are well known in themselves but when made from the polymers of the invention possess new and useful properties. In addition to the required properties such as chemical, physical and thermal inertness, vessel substitutes made from the polymers of the invention possess unusual colloidal properties which permit them to be very closely assimilated to those of living tissue and hence suitable for contact with body tissues for prolonged periods of time. Articles made from the polymers of the invention can be sterilized by boiling and, by steeping them in a physiological solution prior to insertion as a body tissue replacement, can be made isotonic with the surrounding tissue.

An unexpected advantage of articles made from the polymers of the invention is that because of their reversible fluid adsorption properties, heparin, dissolved in isotonic salt solution, or other anticoagulants in a suitable solvent, can be added during manufacture and polymerization in situ can then be effected. The anticoagulant is then present in the vessel substitute for slow release after transplant to prevent thrombic formation. Medicinally-active substances, such as antibiotics and other active substances such as bacteriocides, antivirals, fungicides, which are water or alcohol soluble, may be added prior to polymerization or the end product polymer may be immersed in a solution of such substances to form a carrier.

The mechanical properties imparted to the polymer of the invention and its ability to achieve isotonicity with the surrounding tissue are strongly influenced by the proportion of polyfunctional cross-linking agent present. For the polymers of this invention, concentrations of 0.05 to 15 g./100 g. of 2-hydroxy ethyl or hydroxy propyl methacrylate have been found to be convenient, the preferred range being 0.1 to 1.0 g. cross-linking agent per 100 g. of polymerizable hydroxy alkyl ester.

Prior to casting, the vessel substitutes may be reinforced with strengthening materials such as woven glass fibers, dacron and the like, in various mil and denier sizes present in tubular form in the mold so that the strengthening material is completely encased by the casting solution.

Polymerization of the casting solutions may be accelerated by the application of heat or, by selecting the catalyst and the amount thereof, the application of heat may be omitted and rapid polymerization induced at ambient temperatures. In instances where heat is applied for curing temperatures broadly ranging from about 20°–150°C. are used with ranges from about 20° – 100°C. being found convenient, the preferred range being about 40° –80°C. The reaction preferably is performed in an inert or anaerobic atmosphere employing carbon dioxide or nitrogen. It is known that the presence of oxygen inhibits the polymerization reaction thus requiring a longer reaction time or the use of increased polymerizing temperatures.

Additionally, the polymers of the present invention are particularly adapted for the manufacture of other prosthetic devices such as body implants inasmuch as the liquid casting syrups in prepolymer form can be used for direct in situ polymerization. Contraceptive devices, such as intrauterine implants, diaphragms, and the like are well known in the art. A difficulty commonly encountered in the fabrication of such devices is that the material from which they are made is frequently irritating to such body tissues as mucous membranes. In addition, these devices frequently undergo deterioration on repeated sterilization by boiling water or steam. The difficulties encountered in the prior art may be eliminated by fabrication of contraceptive devices comprised of the polymers of the present invention. In addition to the required properties such as chemical, physical and thermal inertness, the contraceptive devices made from the polymers of this invention possess unusual colloidal properties which permit them to be closely assimilated to living tissue. This permits them to be suitable for contact for prolonged periods of time. In order to obtain a device of suitable rigidity in such instances where this property is desired, it is preferable to blend in a filler material with the casting resin prior to final cure. The filler material may be an inert salt, such as barium sulfate, calcium carbonate, clay and the like. Another means of constructing a tissue compatible contraceptive device is by coating such a device made from another rigid plastic with the polymer composition of the present invention. Such a rigid device may be constructed of nylon, polyethylene, and the like. The poly-hydroxyalkyl ester functions to make the device more compatible with the tissue.

A further use of the present hydrophilic polymers in particulate form such as powders, beads, extrusions and the like, is as a filter medium for tobacco smoke and other gaseous combustion products. The present hydrophilic polymer provides a non-migratory humectant carrier when it is presaturated in a polyhydric alcohol, e.g., glycerine propylene glycol, polypropylene glycol and ethylene glycol. Additionally, the hydrophilic polymers of the present invention provide an excellent industrial filter medium in that they have the ability to retain and release other components, such as thiourea or dithioaerythritol, which are stable against oxidation and are therefore available for reaction with the toxic, irritant or odorous combustion products of the exhaust smoke to eliminate or modify same to nonobjectionable form. Such components need only be soluble in the polyhydric alcohol, alcohol or water which is carried by the hydrophilic filtering medium. Thus, absorption of and reaction with nitrous oxides, hydrocarbons and other combustion products in the gas stream can be had.

The hydrophilic filtering medium additionally can be compounded with tobacco flavoring meterial to fortify or supplement the flavor lost in the train of exhaust tobacco smoke on inhalation through the present filter medium which is capable of removing some of the tars and nitrogenous combustion products which are understood to contribute the desired tobacco flavor. Additionally, specific flavoring materials such as menthol and the like also can be incorporated into the filter material for release into the smoke train so as to improve the taste of the tobacco smoke upon inhalation.

The hydrophilic filter medium of the present invention can be readily employed for use as a chromatographic filter by means of its ability to absorb water soluble pigmented stain or color components.

In another embodiment of the invention the present hydrophilic polymers in powdered form also may be employed as a thickening agent in foods, particularly in view of their ability to take up water when in the dry state.

In still another embodiment of the invention, the hydrophilic gel materials of the present invention may be employed in the form of a covering or bandage carrying medication which can be slowly released from the hydrophilic gel material. Preferably, the bandage is formed of a plastic mesh reinforcement member carrying the hydrophilic gel material in the form of a strip or layer which has been cast thereon.

In still another form of the invention, the hydrophilic gel material is adapted to carry water-soluble nutrients which can be released under controlled conditions. Thus, agar plates can be formed to carry the water soluble nutrient, then dried and available for substantially instant use upon soaking in water.

These and other objects and embodiments of the invention will be readily understood by reference to the following examples which are given by way of illustration without limitation:

EXAMPLE 1

Purified 2-hydroxy ethyl methacrylate is stirred with a cross-linking monomer, ethylene glycol dimethacrylate, in the concentration of 0.15 grams per 100 grams 2-hydroxy ethyl methacrylate. To the mixture is added 90 percent by weight of styrene copolymer resin (a commercial brand resin "Piccoflex" was employed) and 0.15 grams of a free-radical, vinyl polymerization catalyst, isopropyl percarbonate, in an anaerobic atmosphere at ambient temperature. The solution is cast into a mold to form a shaped diaphram which is cured for 30 minutes at 200°C. for approximately 30 minutes and removed from the mold. The diaphram is machined and polished to form a finished article.

EXAMPLE 2

Purified 2-hydroxy ethyl methacrylate is stirred with ethylene glycol dimethacrylate, in the concentration of 0.1 grams per 100 grams 2-hydroxy ethyl methacrylate. To the mixture is added 50 percent by weight of coumarone-indene resin (a commercial brand resin "Cumar" was employed) and 0.15 grams isopropyl percarbonate is added in an anaerobic atmosphere at ambient temperature. The solution is cast onto a steel panel in the form of a film which is cured for 30 minutes at 40°C. to form a thermosetting film characterized by high gloss, adhesion, abrasion resistance, hardness and high impact strength.

EXAMPLE 3

Purified 2-hydroxy ethyl methacrylate is stirred with ethylene glycol dimethacrylate, in the concentration of 0.1 grams per 100 grams 2-hydroxy ethyl methacrylate. To the mixture is added 75 percent by weight of polyvinyl acetate resin (a commercial brand resin "Polyco" was employed) and 0.15 grams benzoyl peroxide is added in an anaerobic atmosphere at ambient temperature. The solution is cast onto a steel panel to form a film which is cured for 30 minutes at 100°C. to form a thermosetting film characterized by high gloss adhesion, abrasion resistance, hardness and high impact strength.

EXAMPLE 4

Purified 2-hydroxy ethyl methacrylate is stirred with ethylene glycol dimethacrylate, in the concentration of 0.05 grams per 100 grams 2-hydroxy ethyl methacrylate. To the mixture is added 50 percent by weight of terpene resin (a commercial brand resin "Piccolyte" was employed) and 0.05 grams isopropyl percarbonate is added in an anaerobic atmosphere at ambient temperature. The solution is cast onto a steel panel to form a film which is cured for 30 minutes at 40°C. to form a thermosetting film characterized by high gloss, adhesion, abrasion resistance, hardness and high impact strength.

EXAMPLE 5

Purified 2-hydroxy ethyl methacrylate is stirred with ethylene glycol dimethacrylate, in the concentration of 0.3 grams per 100 grams 2-hydroxy ethyl methacrylate. To the mixture is added 50 percent by weight of phenolic resin (a commercial brand resin "Durez" was employed) and 0.3 grams isopropyl percarbonate is added in an anaerobic atmosphere at ambient temperature. The solution is cast onto a steel panel to form a film which is cured for 30 minutes at 40°C. to form a thermosetting film characterized by high gloss, adhesion, abrasion resistance, hardness and high impact strength.

EXAMPLE 6

Purified 2-hydroxy ethyl methacrylate is stirred with ethylene glycol dimethacrylate, in the concentration of 1.0 grams per 100 grams 2-hydroxy ethyl methacrylate. To the mixture is added 50 percent by weight of pentaerythritol ester of a rosin derived resin (a commercial brand resin Pentalyn was employed) and 0.2 grams isopropyl percarbonate is added in an anaerobic atmosphere at ambient temperature. The solution is cast onto a steel panel to form a thermosetting film which is cured for 30 minutes at 40°C. to form a film characterized by high gloss, adhesion, abrasion resistance, hardness and high impact strength.

EXAMPLE 7a

Purified 2-hydroxy ethyl methacrylate is stirred with ethylene glycol dimethacrylate in the concentration of 0.1 grams per 100 grams 2-hydroxy ethyl methacrylate. To the mixture is added 50 percent by weight of glycol ester of a rosin resin (a commercial brand resin "Polypale Ester" was empdloyed) and 0.15 grams isopropyl percarbonate is added in an anaerobic atmosphere at ambient temperature. The solution is cast onto a steel panel to form a film which is cured for 30 minutes at 40°C. to form a thermosetting film characterized by high gloss, adhesion, abrasion resistance, hardness and high impact strength.

EXAMPLE 7b

The foregoing process is repeated with a methyl ester of a rosin resin (a commercial brand resin "Abalyn" being employed to replace the resin of the previous example) to result in a thermosetting film.

EXAMPLE 7c

The foregoing process of Example 7a is repeated with a hydroabietyl alcohol (a commercial brand of a balsamic liquid "Abitol" being employed to replace the resin of Example 7a) to result in a thermosetting film.

EXAMPLE 7d

The foregoing process of Example 7a repeated with polycaprolactam (a commercial brand "Nylon-6" was employed to replace the resin of Example 7a) to result in a thermosetting film.

EXAMPLE 7e

The foregoing process of Example 7a is repeated with polysiloxane (a commercial brand resin "GE silicone Resin 84" being employed to replace the resin of Example 7a) to result in a shaped body in the form of a decorative article.

EXAMPLE 8a

Purified 2-hydroxy ethyl methacrylate is stirred with ethylene glycol dimethacrylate, in the concentration of 0.1 grams per 100 grams 2-hydroxy ethyl methacrylate. To the mixture is added 50 percent by weight of phenoxy resin characterized as a high molecular polyhydroxy ether resin prepared from bisphenol A and epichlorohydrin resin (a commercial brand resin "Phenoxy 8500" was employed) and 0.15 grams isopropyl percarbonate is added in an anaerobic atmosphere at ambient temperature. The solution is cast onto a steel panel to form a film which is cured for 30 minutes at 40°C. to form a thermosetting film characterized by high gloss, adhesion, abrasion resistance, hardness and high impact strength.

EXAMPLE 8b

The foregoing process is repeated with low molecular weight polyisobutylene in the range of 8700 to 10,000 m.w. (a commercial brand resin "Vistanex LM-MS" being employed to replace the polyhydroxy ether resin of the foregoing example) to form a thermosetting film characterized by high gloss, adhesion, abrasion resistance, hardness and high impact strength.

EXAMPLE 8c

The foregoing process of Example 8a is repeated with an alcohol soluble protein of corn consisting of globular prolamine having a molecular weight range of 40,000–50,000 (a commercial brand resin "Zein" being employed to replace the polyisobutylene of the foregoing Example 8a) to form a thermosetting film characterized by high gloss, adhesion, abrasion resistance, hardness and high impact strength.

EXAMPLE 9a 2-hydroxy ethyl methacrylate (100 parts) is combined with t-butyl peroctoate (0.05 parts) at 25°C. in an inert atmosphere. This mixture is combined with Nylon-6 (100 parts) in trifluoroethanol (85 parts) to form a clear solution. This is heated at 65° to 70°C. to form a prepolymer. The prepolymer solution is cooled to 25°C and t-butyl peroctoate (0.10 parts) and ethylene glycol dimethacrylate (0.2 parts) is added. The viscous syrup is passed through an extruder having an orifice of 0.01 in diameter. The extruded fiber is passed immediately into a heated water bath, maintained at a polymerizing temperature of 80°C. After 30 minutes the solid fiber is removed from the water, is air dried and oriented at 100°C.

Fabrics made from this fiber are extremely smooth in texture and have a high degree of softness to the touch.

EXAMPLE 9b

The procedure of Example 9 is repeated with the modification that isomeric hydroxy propyl methacrylate is employed in place of hydroxy ethyl methacrylate.

EXAMPLE 9c

The procedure of Example 9a is repeated with the modification that α-cumene hydroxy peroxide is employed as the free-radical vinyl polymerization catalyst.

EXAMPLE 10a 2-hydroxy ethyl methacrylate (50 parts) and $TiO_2$ (30 parts) are ground in a pebble mill to a fine powder (Hegeman 7–8). Additional 2-hydroxy ethyl methacrylate (50 parts) is added along with ethylene glycol dimethacrylate (0.2 parts), cobalt naphthenate a conventional metallic paint dryer or catalyst (0.1 parts) and t-butyl peroctoate (0.4 parts). The resulting viscous syrup is painted onto a wooden boat hull and cured at 20° to 35°C. The resulting protective marine coating is characterized by its ability to discourage barnacle and algae growth and corrosion on prolonged underwater exposure.

EXAMPLE 10b

The procedure of Example 10a is repeated with the modification that the coating syrup is cast onto a steel hull and cured at 100°C. in the absence of cobalt naphthenate.

EXAMPLE 10c

The procedure of Example 10a is repeated employing an isomeric mixture of hydroxy isopropyl methacrylate isomers in place of the hydroxy ethyl methacrylate.

EXAMPLE 11a

A solution comprised of 2-hydroxy ethyl methacrylate (100 parts), ethylene glycol dimethacrylate (0.2 parts), and t-butyl peroctoate (0.4 parts) is cast onto a neoprene rubber sheet and heated at 70°C. for 1 hour. The resulting coated sheet is easily fabricated into a bathing cap form having the aforementioned properties.

EXAMPLE 11b

A solution comprised of 2-hydroxy ethyl methacrylate (100 parts), ethylene glycol dimethacrylate (0.2 parts), and t-butyl peroctoate (0.4 parts) is cast onto a neoprene rubber sheet, covered by a second rubber sheet so as to exclude air, and heated at 80°C. for 1 hour. At the end of this time, both sheets are firmly bonded to one another by the intermediate polymeric layer.

EXAMPLE 12a 2-hydroxy ethyl methacrylate (100 parts) is stirred with 0.05 parts t-butyl peroctoate in a nitrogen atmosphere at a temperature of 40°C. for 30 minutes. The resultant mixture is cooled to 25°C. and t-butyl peroctoate added so as to make the total amount of t-butyl peroctoate added in the system 0.15 parts. Ethylene glycol dimethacrylate (0.1 parts) is added at the same time. The casting solution is poured into molds conforming to the desired shape of an intrauterine device of the type shown in U.S. Pat. No. 3,200,815 and then cured at 70°C.

EXAMPLE 12b

The process of Example 12a is repeated, substituting 0.2 parts of 1,3-butylene glycol dimethacrylate as the cross-linking monomer.

EXAMPLE 13a 2-hydroxy ethyl methacrylate (100 parts) is stirred with distilled water (50 parts) and tertiary butyl peroctoate (0.1 parts), in an anaerobic atmosphere at a temperature of 40°C. for 20 minutes. The resultant mixture is cooled to 25°C. and t-butyl peroctoate (0.05 parts) added. A cross-linking monomer such as ethylene glycol dimethacrylate (0.2 parts) is added at the same time as the catalyst. The casting solution is dip-coated onto polyethylene intrauterine devices of the type shown in U.S. Pat. No. 3,200,815 and cured at 70°C. for 1 hour. Such products exhibiting a tacky or sticky surface are immersed in water to dissolve all the unpolymerized remaining monomer material, thereby effecting a smooth, non-tacky surface.

EXAMPLE 13b

The process of Example 13a, repeated in the absence of water, resulted in a casting solution which upon curing formed a substantially complete (99.5%) polymerized polymer product which exhibited a smooth non-tacky surface.

EXAMPLE 13c

The process of Example 13b is repeated, substituting a mixed catalyst consisting of 0.05 parts t-butyl peroctoate and 0.1 parts isopropyl percarbonate. Catalyst concentration is brought to theoretical by addition of isopropyl percarbonate.

EXAMPLE 13d

The procedure of Example 13b is repeated with the modification that $BaSO_4$ (50 parts) is blended with the polymer system prior to casting and final cure.

EXAMPLE 14a

Distilled 2-hydroxy ethyl methacrylate (100 g.) is stirred with 0.1 g. tertiary butyl peroctoate in an anaerobic atmosphere at 25°–70°C. for 15–40 minutes. The resultant mixture is cooled to 25°C. and tertiary butyl peroctoate added so as to make the total concentration of tertiary butyl peroctoate in the system 0.2/100 grams of 2-hydroxy ethyl methacrylate. Ethylene glycol dimethacrylate, in the concentration of 0.2 g./100 g. of 2-hydroxy ethyl methacrylate is added at the same time as the catalyst concentration is brought up to the theoretical content. Micro silica of particle sizes 0.15 – 0.02 microns (commercial "Cab-O-Sil") is post added to the casting syrup to yield a prepolymer syrup of desired rheological properties for use as a denture liner base material. The casting syrup may be spread on a standard polymeric acrylic denture base material and, after being impressed, polymerized with same in a single polymerizing process in a standard molding flask under standard conditions of time, temperature and pressure. In the case of existing polymerized denture bases, the casting syrup may be spread thereon and, after being impressed, polymerized under standard denture molding conditions, the latter being disclosed in U.S. Pat. No. 2,645,012. Casting syrups for in situ polymerization to form various articles having specific desired properties such as mechanical strength, high reversible fluid absorption properties, shape retention in fluid media and elasticity recovery after deformation are thereby formed.

EXAMPLE 14b

The process of Example 14a is followed, substituting hydroxy propyl methacrylate for the 2-hydroxy ethyl methacrylate monomer.

EXAMPLE 14c

The process of Example 14a is followed using isopropyl percarbonate as the catalyst and substituting 1,3-butylene glycol dimethacrylate as the cross-linking monomer.

EXAMPLE 14d

The process of Example 14a is followed with the exception that an integral mouth guard impression is molded from an impression by use of the said casting syrup. If desired, a reinforcing center element of rubber may be dip-coated with the casting syrup so as to provide additional rigidity.

EXAMPLE 15a 2-hydroxy ethyl methacrylate (100 g.) is mixed with tertiary butyl peroctoate in the quantity 0.15 g./100 g. methacrylate. Ethylene glycol dimethacrylate, in the concentration of 0.20 g./100 g. 2-hydroxy ethyl methacrylate is added along with 1 gm. of a foaming agent, sodium bicarbonate. The mixture is heated to 70°C and the resulting solid, friable polymeric foam is ground into fine power of 80 mesh. The polymeric powder so formed is mixed with a natural anise flavor solution and the resultant mixture is placed on a mechanical roller for approximately 8 hours. The polymeric powder thus absorbs the flavor. The solution is then filtered and the residue dried at room temperatures.

EXAMPLE 15b

The process of the previous Example 15a is followed, substituting an oil of orchids perfume essence for the anise flavor.

EXAMPLE 16

2-hydroxy ethyl methacrylate (100 g.) is mixed with tertiary butyl peroctoate (0.20 g.). Ethylene glycol dimethacrylate (0.20 g.) is added along with 4 g. of a foaming agent, sodium bicarbonate. The mixture is heated to 70°C. and the resulting solid, friable polymeric foam is ground into fine powder of 80 mesh. The polymeric powder formed is mixed with a sufficient amount of phenoxymethyl penicillin antibiotic dissolved in ethyl alcohol to provide for gradual release of 1,200,000 units per gram, and the resultant mixture placed on a mechanical roller until the polymeric powder has absorbed the desired concentration of antibiotic. The solution is then filtered and the residue dried in vacuo.

EXAMPLE 17

Suitably purified 2-hydroxy ethyl methacrylate is stirred with 0.15 g. isopropyl percarbonate in an anaerobic atmosphere at ambient temperature. Ethylene glycol dimethacrylate in the concentration of 0.1 g./100 g. 2-hydroxy ethyl methacrylate is added. Heparin, an anti-coagulant, is added before casting. The solution is cast into a tube or mold of known vessel thickness and diameter containing a dacron tubularly shaped strengthening material so that in use, stitching of the vessel substitute to the vessel being repaired is facilitated. The strengthening material is completely encased by the casting solution. Insertion of an appropriately sized mandril into the mold yields an arterial vessel of the desired wall thickness. The shaped article is then cured 30 minutes at 40°C., removed from the mold, washed with water and subsequently stored in an aqueous solution.

EXAMPLE 18a 100 g. of 2-hydroxy ethyl methacrylate is mixed with 0.15 g. tertiary butyl peroctoate. 0.2 g. ethylene glycol dimethacrylate is added, along with 1 g. of sodium bicarbonate. The mixture is heated to 70°C. and the resulting polymer is disintegrated into pellet size particles by grinding and shearing. The pellets are mixed in a 50–50 mixture of glycerine and water for 8 hours to provide a non-migratory humectant action and dried. The resulting pellets are employed as a tobacco smoke filter in a cigarette.

EXAMPLE 13b

The process of the preceding example is repeated with the exception that tobacco flavor is added to the glycerine-water mixture to impart a tobacco flavor to the filtered smoke to replace the flavor lost by filtration of the tars and other combustion products which normally impart the tobacco flavor upon inhalation.

In a further embodiment, an alcoholic solution of menthol was employed as a flavoring agent along with the tobacco flavor. The alcoholic solutions may be employed so as to result in amounts ranging fron 1 to 90 per cent by weight of the hydrophilic polymer, although 10 per cent is preferred, particularly if glycerine is employed as the humectant.

EXAMPLE 18c 100 parts 2-hydroxy ethyl methacrylate is stirred with 0.05 parts tertiary butyl peroctoate in a nitrogen atmosphere at a temperature of 30°C. for 30 minutes. The resultant mixture is cooled to 25°C. and additional peroctoate is added to make up a total of 0.15 parts, 0.1 parts ethylene glycol dimethacrylate being added at the same time. The casting solution is poured onto a plate in the form of a film and cured at 70°C. for 30 minutes to result in a chromatographic filter element capable of absorbing water soluble stain and color components such as water-soluble pigmented bodies of synthetic and natural color dyes and the like.

EXAMPLE 19

100 g. 2-hydroxy ethyl methacrylate is mixed with 0.20 g. tertiary butyl peroctoate in an inert atmosphere and 0.20 g. ethylene glycol dimethacrylate is added. Water-soluble catalyst is added to the mixture before casting at 40°C. for 30 minutes to form a catalytic bed support. The dried support, when wet with water, is adapted to release the catalyst in an aqueous solution or wet gas stream to be catalyzed.

EXAMPLE 20a 100 g. 2-hydroxy ethyl methacrylate is stirred with 0.15 g. isopropyl percarbonate in an anaerobic atmosphere at ambient temperature. 0.1 g. ethylene glycol dimethacrylate is added. Before casting, a 2% aqueous solution of Merbromin is added as a general antiseptic. The resulting solution is cast onto a dacron mesh cloth in the form of a film to result in a bandage form upon curing for 30 minutes at 40°C. The dried bandage, upon being wetted by immersion in water, or on contact with the lymphatic exudate of an open wound or with mucous membrane, gradually releases the antiseptic.

EXAMPLE 20b

A sheet or film in bandage form is made in accordance with Example 20a having a thickness range from about 5 mils to 1.5 mm. In place of the general antiseptic the topical antibiotic neomycin sulfate is added before casting in an amount of 5 mg. (equivalent to 3.5 mg base) per gram of polymeric carrier. The resultant film is employed as a temporary covering for burns, it being found that the antibiotic loading of the polymer in contact with flesh burns prevents the dreaded complication of pseudomonas injection and septicemia as well as limiting fluid loss from the burn surface.

EXAMPLE 21

100 g. 2-hydroxy ethyl methacrylate is stirred with 0.1 g. tertiary butyl peroctoate in an inert atmosphere and 0.15 g. ethylene glycol dimethacrylate is added. Before casting at 40°C. for 30 minutes, nutrient media is added to make up 50% by weight of the polymer solution. The dry plate can be stored and thereafter immersed in water to release nutrient media for immediate staining for bacterial cultures.

EXAMPLE 22

The process of Example 12a is repeated, the casting solution being poured into molds conforming to the shape of a contact lens button which, after cooling and drying, can be ground by conventional means to form toric contact lenses. By compensating for the volumetric increase of about 18 per cent resulting from wetting the lens after grinding, the grinding operation can be performed accurately to give the desired dimensions.

EXAMPLE 23

The process of Example 12a is repeated, the casting solution being poured into molds conforming to the shape of the desired prosthetic devices and body implants.

EXAMPLE 24

Bristles adapted for use in tooth brushes, cleansing brushes, and the like may be prepared by the process described in Example 9. If additional strength is desired for the bristles, they may be formed with an axial fiber of nylon or the like and dip-coated as described in the foregoing Example 14d, the reinforcing center element being of rubber, plastic or the like.

EXAMPLE 25a

The casting solution prepared in accordance with Example 12a is employed as a base stock casting solution or syrup to which oil of peppermint, a flavoring agent, is added in an amount of 10 parts. The flavored casting solution is set aside and can be employed as desired to form cast products in the form of shaped bodies or in powdered form. In a further embodiment, the flavoring agent is added along with the makeup catalyst.

EXAMPLE 25b

The casting solution of Example 13a is employed as a base or stock solution to which oil of orchids perfume essence (10 parts) is added. The resulting perfume carrying stock solution is set aside for later employment as a casting solution or syrup to form upon curing a shaped body in the form of an artificial flower decoration adapted for use as a decorative package attachment for a perfume bottle.

EXAMPLE 25c

The casting syrup of Example 14a is prepared without the employment of micro silica. In place of the latter, an alcoholic solution of menthol (10 parts) is added to the casting syrup to yield a mentholated prepolymer casting syrup.

EXAMPLE 25d

The casting syrups of Examples 12a, 13a and 14a are employed as base casting syrups to which a water-soluble stain and color, a synthetic color dye and a natural color dye, respectively are added to the base preparations to form a stock solution for later casting or other use.

EXAMPLE 25e

The casting solution of Example 17 is prepared and in place of the anti-coagulant heparin, the antibiotic phenoxymethyl penicillin of Example 16, dissolved in ethyl alcohol, is added in an amount to provide for gradual release of 1,200,000 units per gram of casting syrup. The resulting casting syrup is set aside as a stock solution for later casting or other use. The casting syrup and the resulting cast product either in shaped or powdered form are employed as a pharmaceutical carrier for the antibiotic. The use of the casting syrup or resulting shaped or powdered preparation has the advantage that it prevents deterioration and loss of potency to which the antibiotic is subject in conventional pharmaceutical carriers, thereby extending the shelf life or expiration date of the antibiotic preparation. In addition, the hydrophilic polymer prepared in accordance with the present invention has the desirable characteristics, whether dry or solvent filled, of preventing the imbibition with microbial and fungal contaminants, such as gram negative and gram positive microorganisms, yeast, molds and viruses. This characteristic is of particular importance in the presence of contaminants, such as preventing contamination of penicillin with various yeast forms.

EXAMPLE 26

Distilled 2-hydroxy ethyl methacrylate (100 g.) is stirred with 0.05 tertiary butyl peroctoate in an anaerobic atmosphere at 25°–70°C. for 14–40 minutes. The resultant mixture is cooled to 25°C. and tertiary butyl peroctoate added so as to make the total concentration of tertiary butyl peroctoate in the system 0.15/100 grams of 2-hydroxy ethyl methacrylate. Ethylene glycol dimethacrylate, in the concentration of 0.15 g./100 g. of 2-hydroxy ethyl methacrylate is added at the same time as the catalyst concentration is brought up to the theoretical content. Oil of peppermint flavoring (11.10 parts) is also added to the casting syrup to yield a flavored prepolymer syrup which is suitable for storing. After curing and granulation, the flavor carrying granules are added as a flavoring releasing component to chewing gum, gelatin and antacid tablets.

EXAMPLE 27

Ninety grams of a stock casting syrup, made in accordance with Example 14a, is added under stirring 0.15 g. tertiary butyl peroctoate in an anaerobic atmosphere at 25°–70°C. for 15–40 minutes, the amount of monomer employed being adjusted to result in 90 g. final casting syrup. The resultant mixture is cooled to 25°C. and tertiary butyl peroctoate added so as to make the total concentration of tertiary butyl peroctoate in the system 0.15/100 grams of 2-hydroxy ethyl methacrylate. Ethylene glycol dimethacrylate, in the concentration of 0.15 g./100 of 2-hydroxy ethyl methacrylate, is added at the same time as the catalyst concentration is brought up to the theoretical content. Oil of peppermit (10 g.) is added to the casting syrup to form a flavored stock solution.

EXAMPLE 28

The casting syrup of Example 14a is employed as a base solution to which is added ethynodiol diacetate as the progestagen component plus mestranol as the estrogen component in an amount sufficient to provide a timed daily release time of 10 to 1 parts by weight, respectively, when the casting syrup is prepared in the form of a shaped body or in powdered form. The resulting preparation is used as a body implant, or tablet for oral administration for contraception or in other therapy for fertility regulation or disturbance. One advantage of the use of the instant hydrophilic polymers as pharmaceutical carriers is that it permits a desired slow release or timed release of the active component. The release time is adjusted readily by the amount of cross-link agent employed, the surface to volume ratio of the formed plastic, and the concentration or concentration gradient of the biologically active substance so incorporated. Release rate is increased by inclusion of solvent in the casting solution.

EXAMPLE 29

Purified 2-hydroxy ethyl methacrylate (100 g.) is mixed with 0.2 g. of ethylene glycol dimethacrylate and 1 g. of benzoyl peroxide. The monomer solution is sprayed via a nozzle which forms fine droplets into a chamber containing nitrogen at a temperature of 150°C. After spraying of the monomer was concluded, 36 g. of polymer beads suitable for impregnation by flavors or scents was recovered from the floor of the chamber.

EXAMPLE 30

Purified 2-hydroxy ethyl methacrylate (100 g.) is mixed with 15 g. of ethylene glycol dimethacrylate, 10 g. of orange oil and 0.3 g. of tertiary butyl peroctoate. The solution is poured into a 250 ml. polypropylene beaker which is placed in an oven under a nitrogen atmosphere at 80°C. for 3 hours to effect polymerization. The cast cylinder so obtained is friable, and can easily be comminuted to a powder which rapidly releases the orange oil in contact with hot water.

EXAMPLE 31

In 3 cc. of 2-hydroxy ethyl methacrylate containing 0.2% of ethylene glycol dimethacrylate and 0.15% tertiary butyl peroctoate was dissolved 100 milligrams of norethandrolone (Nilevar). The solution was cast in the form of a cylinder 1 cm. 3 cm. and was polymerized at 80°C. for 3 hours in a nitrogen atmosphere. After removing from the mold, a cylinder suitable for in vivo implantation to provide prolonged release of the norethandrolone (Nilevar) was obtained for use in animal husbandry.

EXAMPLE 32

Raw cotton suture thread is immersed in the casting syrup of Example 14a with thickening agent omitted and is passed through a polymerization zone having a nitrogen atmosphere maintained at 100°C. Residue time in the zone is held at 1½ hours. The coated, impregnated suture so obtained in soaked in an alcoholic solution of fluorothiouracil and penicillin, and is then dried. The surgical suture thus obtained is beneficial in preventing spread of infection and spurious cell migration along suture lines during post-operative healing.

EXAMPLE 33a

A rubber Foley catheter is immersed in the casting syrup of Example 14a with the thickening agent omitted, and then is removed and subjected to a temperature of 80°C. in an inert atmosphere to effect polymerization of the coating thus applied. The coated catheter is then immersed in an aqueous solution of neomycin sulfate and is then dried to provide a catheter effective in preventing infections when used in the urinary tract.

EXAMPLE 33b

A tube of Example 34 5 cm. in length with an outer diameter of 3 mm. and a wall thickness of 0.8 mm. is fitted at each end with a teflon felt collar adhered thereto by Silastic (silicone) adhesive. The device is employed to join the severed ends of a ureter by suturing the ends thereof to the teflon collars. Segmented ureter replacements in the dog have functioned satisfactorily for over 6 months and upon sacrifice no encrustations were observed within the lumen of the polymer.

EXAMPLE 33c

The process of Example 33a is employed to coat tubes of various sizes for use as vessel grafts and substitutes, common ducts, urethral replacement segments and lung tracheal segments. It has been found that venus tubes deep-coated with ethyl alcohol solutions of the polymer preparations of Example 34 can be placed in the inferior and superior of the vena cava for extended periods whereas uncoated plastic tubes ordinarily clot in the venous stream within minutes. Such dipcoating can be applied to thrombogenic plastics to body insert materials and heart valve component fabrication. The polymer solution of Example 33a in aqueous ethyl alcohol also is adapted to be cast in situ as a film on moist internal body surfaces as by brushcoating on the abraded surfaces of bowel to deter adhesion formation.

EXAMPLE 34

100 g. of casting syrup of Example 33a was added to three times its volume of water with vigorous agitation. The white precipitate so obtained was isolated by filtration and dried to yield 9.0 g. of polymer showing an intrinsic viscosity of 1.03 when dissolved in absolute methanol. The polymer, as dissolved in methanol, is suitable for the formation of hydrophilic coatings and films by spray coating, dip coating, casting and the like.

The resulting cast polymer exhibited controlled hydrophilic properties being incapable of absorbing more than 30% water when equilibrated in aqueous medium.

EXAMPLE 35

The solution of Example 17 is used to bond heparin through absorption of benzalkonium chloride as reported in Gott's technique (J. Surg. Research — Vol. 6, p. 274, 1966).

Shaped articles of the hydrophilic polymer solution of Example 33a also can be employed for ion transfer in hemodialysis for the incorporation of the hemostatic agent thrombin and as carriers for estrogens; nitrogen mustard, parathormone, the transport of edema fluid and for the export of oxygen saturated solutions to a blood-plastic interface in artificial lung applications. Pellets or discs of the instant polymeric material can be soaked in oral antiseptic solutions and can be employed in the oral cavity, particularly in the buccal pouch or in the sublingual cavity for the slow release of the oral antiseptic as a breath sweetener.

EXAMPLE 36a

Into a flask equipped with an agitator and a heating mantle was charged 1000 grams of silicone oil; 100 grams of 2-hydroxy ethyl methacrylate and 0.33 grams of isopropyl percarbonate. The flask was placed under a nitrogen atmosphere and the contents were rapidly agitated and heated to 100°C. After 15 minutes at 100°C., the polymer slurry obtained was filtered hot to isolate the polymer. The polymer powder was reslurried in 300 ml. of xylene, filtered and dried. A 98% yield of 2 $\mu$ to 5 $\mu$ particle size powder was obtained. The powder was employed in the injection molding and extrusion of shaped articles. Additionally, the powder was dissolved in ethanol to form solutions for casting hydrophilic polymer films.

EXAMPLE 36b

Example 36a was repeated using mineral oil in place of the silicone oil. The amount of 2-hydroxy ethyl methacrylate was increased from 100 g. to 200 g. and the quantity of isopropyl percarbonate was increased from 0.33 to 0.66 g. A 98% yield of polymer beads ranging in diameter from 2 to 5 microns was obtained.

EXAMPLE 36c

Examples 36a was repeated using xylene, in place of the silicone oil. The amount of 2-hydroxy ethyl methacrylate was increased from 100 g. to 300 g. and the quantity of isopropyl percarbonate was increased to 0.99 g. An 85% yield of polymer beads was obtained.

EXAMPLE 37

Poly- (2-hydroxy ethyl methacrylate) 30 g., prepared in accordance with Example 36a, was dissolved in 70 ml. of methanol. To the solution was added 4.0 g. of peppermint oil. The viscous solution was coated on an impervious plate and allowed to dry to form a film 1.0 mil thick. The dry film was stripped from the plate and was ground to form minute platelets suitable for incorporation in food products, chewing gum and toothpaste to provide prolonged release of the peppermint flavor on contact of the product with an aqueous medium. When equilibrated in aqueous medium the platelets were characterized by controlled hydrophilicity, being incapable of absorbing in excess of 30% by weight of water.

EXAMPLE 38

Example 37 was repeated with the following flavoring materials:

| | |
|---|---|
| anethole | citral |
| ethyl propionate | ethyl acetate |
| acetaldehyde | biacetyl |
| menthol | spearmint |
| expressed orange oil | tobacco extract |

Powders were obtained for incorporation in and on articles appropriately suited for the particular flavor incorporated in the powder to provide for controlled release of the flavoring material upon and during wetting of the powder.

EXAMPLE 39

Poly- (2-hydroxy ethyl methacrylate), 50 grams, prepared in accordance with Example 36a, was dissolved in 50 ml. of methanol to form a viscous dope; menthol, 12.5 g., was dispersed in the dope which was then forced through a spinaret to form fine filaments which were permitted to dry and thereafter were chopped to a fine powder for use in flavored products.

EXAMPLE 40

To 100 ml. of the athanolic solution of Example 36a was added 2.5 ml. of biacetyl. The solution was sprayed via a nozzle into a heated chamber having a high velocity air flow to effect spray drying of the solution. Particles ranging in size from 2–15 microns in diameter were recovered from the spray drying apparatus. These particles were suitable for incorporation in food products to provide controlled release of the biacetyl flavor, and to prevent oxidation, deterioration or volatilization of the flavor during storage.

EXAMPLE 41

3.6 grams of the powder of Example 36a is impregnated with 0.008 g. of N,N-dimethyl aniline by wetting the powder with an acetone solution of dimethyl aniline and allowing the mixture to dry.

In a separate container, 9.9 g. of 2-hydroxyethyl methacrylate is mixed with 0.0214 grams of ethylene glycol dimethacrylate and 0.05 grams of benzoyl peroxide.

3.6 g. of the impregnated powder, when mixed with 9.9 g. of the formulated hydroxyethyl methacrylate mixture formed a paste mixture which cured within 30 minutes with no applied heat to form a hydrophilic plastic article.

This mixture before cure was used to line a denture without the necessity of using a molding flask and without applied heat and pressure as employed in Example 14a. The mixture before cure was applied to a standard acrylic denture base material, and with the aid of a barrier film or bag, the denture was placed in the mouth to form the impression of the gum and was permitted to cure in the mouth. A total curing time of 10 minutes was used, with 5 minutes curing time taking place in the mouth. The denture liner thus applied exhibited the properties of the denture liner of Example 14a.

Prepared ratios of liquid monomer to powder are from about 2 to 1 to about 4 to 1. Catalyst and activator amounts can be varied to adjust the curing time and exothermic temperatures. As will be apparent, the instant process and formulation enables chair-side preparation and cure of the denture liner directly on the gum of the patient to achieve an exact profile and fit.

EXAMPLE 42

Discs of hydrophilic polymer, prepared as shaped articles from the solution of Example 34, measuring ¼ inch in diameter and 0.5 mm. in thickness were saturated with an antibiotic solution of lincomycin hydrochloride monohydrate (Lincocin) and tested against standard staphylococcic strains on agar plates. The zones of inhibition were compared with standardized 1 mg. discs obtained from the manufacturer. Multiple transfers of the hydrophilic polymer also were made on blood agar to determine how long the elution of the antibiotic from the gel would take place.

It was observed that inhibition of the standard bacterial strain occurred up to 22 days. Comparable paper discs with the same antibiotic exhibited zones of inhibition only for 48 hours. In some cases 6 transfers of the discs, each to a fresh blood agar plate, were carried out. From the results it was apparent that the elution of the agent from the hydrophilic polymer disc is a gradual process and extends over a significant period of time. Moreover, it appears that it is possible to heavily saturate the gel with the desired agent.

EXAMPLE 43

Shaped articles made in accordance with Example 23 in the form of irregular cylinders and blocks were implanted within the right atrial chamber of the dog in order to determine the blood vascular compatibility of the hydrophilic polymer. Upon sacrifice of the dogs, after one month, it was apparent that the hydrophilic polymer did not foster thrombosis and that the only clot observed was at the point of attachment of the hydrophilic polymer article to the atrial wall.

In an in vitro study, glass test tubes coated with methyl alcohol solutions of the hydrophilic polymer made in accordance with Example 37, were filled with canine blood and clotting times were observed. It was noted that as against the controlled clotting times of 6 minutes the hydrophilic polymer coated tubes clotted at an average of 3.5 hours, thereby evidencing that the hydrophilic polymer discouraged surface thrombogenesis.

Additional desired vascular substitute properties exhibited by such implants include wettability, lubricity, conductivity, distensibility and the capability of absorbing and transporting ions of organic and inorganic compounds at high concentration and high rates of transfer including chlorine, sodium, potassium, and phosphate ions.

EXAMPLE 43a

A glass plate for use as a vehicle windshield, window or mirror was coated with a methyl alcohol solution of the hydrophilic polymer made in accordance with Example 37. The resulting coating (0.005 inches thick) was light-transmitting and optically clear, adherent, and did not fog upon exposure to hot moist air. Similarly, a plastic plate of methyl methacrylate for use as an aircraft windshield was so coated.

EXAMPLE 43b

The procedure of Example 43a was followed to coat an optical element in the form of a camera lens having a reflection-reducing film of magnesium fluoride thereon to form a light-transmitting, optically clear, reflection-reducing, non-fogging optical element.

EXAMPLE 44

To the ethanolic solution of Example 36 was added the antibiotic chloramphenicol and the resulting solution was employed to coat a nylon suture.

EXAMPLE 45

To the ethanolic solution of Example 36a was added an alcoholic solution of Mercurochrome. The resulting solution was applied by spraying as a wound dressing.

EXAMPLE 46

3.6 grams of powder of Example 36a is impregnated with Mercurochrome from an acetone solution. The powder is then dried and dusted on a wound as a dressing to provide antiseptic action.

The foregoing examples are directed primarily to the in situ addition of dyes, pigments, thickening agents, resins, medicinally-active substances, bacteriocides, anti-virals, fungicides, strengthening materials, antiseptics, catalyzers, nutrient media, anti-coagulants, steroids and the like during the casting syrup preparation after the initial step in which the water-soluble uncrosslinked homopolymer of the polyhydroxy ethyl methacrylate or the like is formed and preferably at the stage of addition of the makeup catalyst. However, certain additive components, particularly pigments, thickening agents, resins and the like can be added directly to the initial monomer or during the initial polymerization.

We claim:

1. A denture liner composition consisting essentially of an anhydrous mixture of a solid polymer prepared by rapid agitation of a water-soluble polymerizable hydroxyalkyl monoester of acrylic acid of methacrylic acid with a minor amount of a polymerizable diester of acrylic acid or methacrylic acid with an alcohol having at least two esterifiable hydroxyl groups in the presence of an amount of a free-radical, vinyl polymerization catalyst sufficient to polymerize the same while suspended in a form of small droplets in a non polar a suspending medium in which said polymer so formed in insoluble and a monomeric liquid consisting essentially of a major portion of a polymerizable water-soluble hydroxy-alkyl monoester of acrylic acid or methacrylic acid with a minor amount of a polymerizable diester of acrylic acid or methacrylic acid with an alcohol having at least two esterifiable hydroxyl groups in the presence of a free-radical, vinyl polymerization catalyst.

2. A denture liner composition according to claim 1 wherein said monoester is a hydroxyalkyl acrylate or methacrylate having two to three carbon atoms in the alkyl group.

3. A denture liner composition according to claim 2 wherein the monoester is hydroxyethyl methacrylate and the amount of said diester is up to 15 parts per 100 parts of monoester.

4. A denture liner composition according to claim 3 wherein there is also included an amine accelerator.

5. A denture liner composition according to claim 3 wherein the suspending medium is silicone oil or mineral oil and the diester is present in an amount of at least 0.05 parts per 100 parts of monoester.

6. A denture liner composition according to claim 1 wherein the diester is employed in an amount of 0.05 to 15 grams per 100 grams of monoester.

7. A denture liner according to claim 6 wherein the diester is a diester of ethylene glycol and acrylic acid or methacrylic acid.

8. A denture liner according to claim 7 wherein the ratio of liquid monomer to solid polymer is from about 2 to 1 to about 4 to 1.

9. A denture liner according to claim 8 wherein the solid polymer is in the form of a powder.

10. A denture liner according to claim 6 wherein the ratio of liquid monomer to solid polymer is from about 2 to 1 to about 4 to 1 and the solid polymer is in the form of a powder.

* * * * *